United States Patent
Koshida

(12) 
(10) Patent No.: US 6,372,890 B1
(45) Date of Patent: Apr. 16, 2002

(54) WATER-SOLUBLE POLYPEPTIDES

(75) Inventor: Shogo Koshida, Kanagawa (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 09/308,388

(22) PCT Filed: Nov. 18, 1997

(86) PCT No.: PCT/JP97/04195

§ 371 Date: May 18, 1999

§ 102(e) Date: May 18, 1999

(87) PCT Pub. No.: WO98/22505

PCT Pub. Date: May 28, 1998

(30) Foreign Application Priority Data

Nov. 18, 1996 (JP) .............................................. 8-306056

(51) Int. Cl.[7] ........................ C07K 14/475; C07K 1/13; C12N 5/00
(52) U.S. Cl. ........................ 530/350; 530/402; 530/411; 435/325
(58) Field of Search ........................ 424/198.1; 514/12; 530/350, 411, 402; 435/325

(56) References Cited

U.S. PATENT DOCUMENTS 5,726,298 A * 3/1998 Hirai et al. ................. 536/23.5
6,127,149 A * 10/2000 Hirai et al. ................. 435/69.7

FOREIGN PATENT DOCUMENTS

| EP | 562123 | 9/1993 |
|---|---|---|
| EP | 698666 | 2/1996 |
| EP | 837129 | 4/1998 |
| JP | 6-25295 | 2/1994 |
| JP | 6-293800 | 10/1994 |
| JP | 8-325293 | 12/1996 |
| JP | 9-65885 | 3/1997 |

OTHER PUBLICATIONS

Sakurai et al. In vitro branching tubulogenesis: implications for developmental and cystic disorders, nephron number, renal repair, and nephron engineering. Kidney Int. 1998 Jul;54(1):14–26.*

Nathan et al. Cytokines in context. Journal of Cell Biology, (Jun. 1991) 113 (5) 981–986.*

Bowie et al. Deciphering the message in protein sequences: tolerance to amino acid substitutions. Science, (Mar. 16, 1990) 247 (4948) 1306–10.*

Ngo et al., in The Protein Folding Problem and Tertiary Structure Prediction, Merz and Le Grand (Eds), Aug. 1994, Springer Verlag, pp. 433 and 492–495.*

"Epimorphin: A Mesenchymal Protein Essential for Epithelial Morphogenesis", Y. Hirai et al., Cell, vol. 69, May 1, 1992, pp. 471–481.

* cited by examiner

Primary Examiner—David S. Romeo
(74) Attorney, Agent, or Firm—McDermott, Will & Emery

(57) ABSTRACT

In this invention there are provided a polypeptide having morphogenesis-accelerating activity or cell-proliferating activity against epithelial cells, said polypeptide being defined by the 1st to 103rd amino acids from the N-terminal of human epimorphin or being defined by the 1st to 104th amino acids from the N-terminal of murine epimorphin, and a medicament containing said polypeptide as an effective ingredient. Such polypeptides are soluble in water and are useful as the effective ingredients of medicaments for the treatment or prevention of diseases involving the aberration of morphogenesis, such as inflammatory disorders, burn or wound, and as those of medicaments for use in hair growth promotion.

6 Claims, 11 Drawing Sheets

WATER-SOLUBLE POLYPEPTIDES

This application is the National Phase of PCT International Application No. PCT/JP97/04195, filed on Nov. 18, 1997.

TECHNICAL FIELD

This invention relates to novel water-soluble polypeptides having morphogenesis-accelerating activity and cell-proliferating activity against epithelial cells.

BACKGROUND ART

It is suggested that factors derived from mesenchyme cells existing around an epithelial tissue control the normal morphogenesis of the epithelial tissue. It is also recognized that many of the causes of diseases resulting from the abnormal morphogenesis of epithelial tissues are due to the aberration of mesenchyme cells. Based on such findings, there is interest in the elucidation of control mechanism of the morphogenesis of the epithelial tissue by the mesenchyme cells. However, since a group of substances participating in the control of morphogenesis of epithelial tissues by mesenchyme cells is expressed in a complex system under time and spatial restrictions, great difficulty exists in the isolation of these substances and the analysis of their functions. It is also difficult to construct a model experimental system that simplifies the morphogenesis of epithelial tissues. For these reasons and others, there has not been major progress in the studies of this field to date. Accordingly, it is earnestly desired that the control mechanism of morphogenesis of epithelial tissues be analyzed in order to elucidate the mechanism of crisis of diseases resulting from the morphogenesis of the epithelial tissues or to establish methods for the treatment of these diseases.

Under these circumstances epimorphin, which participates in the control of morphogenesis of epithelial tissues, was separated and purified. (Japanese Unexamined Application Publn. Hei 6-25,295.) It was shown that this substance is a physiologically active substance the core protein of which is a protein comprising from 277 to 289 amino acids and which is mainly biosynthesized by mesenchyme cells. It was also shown that epimorphin possesses an activity for accelerating the morphogenesis of epithelial tissues by acting the epithelial cells and that the normal morphogenesis does not take place under conditions where epimorphin does not exert its functions.

In addition, with respect to the structural characteristics of epimorphin, it has been found that structurally the epimorphin molecule is largely divided into four fragments. (European Patent Application Publn. No. 0698666.) Specifically, the polypeptide constituting the full-length epimorphin can be divided into, from its N-terminal side, a coiled coil domain (1), a functional domain (2), a coiled coil domain (3), and a hydrophobic domain at its C-terminal. As for the functional domain among these fragments (the domain defined by the 104th to 187th amino acids from its N-terminal in human epimorphin), it has been suggested that this domain participates in cell adhesion and is closely involved in manifestation of the biological activities of epimorphin. (European Patent Application Publn. No. 0698666 vide supra.)

Since epimorphin possesses an activity for accelerating the normal morphogenesis, it is expected that this substance is useful as a medicament for the prevention or treatment of diseases resulting from the aberration of morphogenesis, or as the active ingredient of medicaments such as a hair growth-promoting agent. However, native epimorphins obtained from mammals find difficulty in being put to practical use as medicaments, because they are sparingly soluble in aqueous media such as physiological saline solution. For this reason, attempts are made to de novo synthesize epimorphin derivatives that are excellent in water-solubility while substantially maintaining the morphogenesis-accelerating activity of the native epimorphins. For example, there is known an altered form (Fragment 123) that is obtained by deletion of the hydrophobic domain at the C-terminal. (Japanese Unexamined Application Publn. Hei 6-25,295.)

With respect to the coiled coil domain (1) which is a partial structure of epimorphin, it has previously been shown that this domain possesses an activity of endowing epimorphin with its solubility. However, it has also been shown that if part of the coiled coil domain (1) is removed by deletion of amino acids from the N-terminal of epimorphin, the cell adhesion activity of the resulting altered form has diminished. (European Patent Application Publn. No. 0698666.) More specifically, it has been disclosed that with regard to the activity of this domain, it positively contributes to the aspect of solubility by such activity as that altering a higher structure of Fragment 23 but that it negatively contributes to the cell adhesion activity by such activity as that masking the functional domain (2); and there has been a negative suggestion concerning the applicability in medicaments. Further, while there have been reports of the cell adhesion activity of each domain of the epimorphin (the coiled coil domain (1), the functional domain (2), or the coiled coil domain (3)) with respect to its physiological activity, the morphogenesis-accelerating activity similar to that of epimorphin has not been known thus far.

DISCLOSURE OF THE INVENTION

An object of this invention is to provide a water-soluble polypeptide having morphogenesis-accelerating activity against epithelial cells. More specifically, it is the object of the invention that a polypeptide be provided which acts on the epithelial cells to accelerate the morphogenesis of epithelial tissues and which is soluble in an aqueous medium such as physiological saline solution.

Another object of this invention is to provide a medicament that contains a polypeptide having the above-mentioned characteristics as an effective ingredient and that is useful for the prevention and/or treatment of a disease which results from of morphogenetic factors such as epimorphin or which involves the destruction of tissue or organ. A further object of the invention is to provide a hair growth-promoting agent containing the above-mentioned water-soluble polypeptide as an effective ingredient.

The present inventors made thorough efforts to attain the above-mentioned objects, and as a result, discovered that polypeptides comprising the coiled coil domain (1), which constitutes epimorphin, are soluble in aqueous media, act on epithelial cells to accelerate the morphogenesis of epithelial tissues, and possess marked cell propagation-accelerating activity against the epithelial cells. This invention has been accomplished based on the above-mentioned findings. As used herein, "cell propagation—accelerating activity" means that when cells are cultured in a serum-free medium for several days, it can increase the number of the viable cells. Namely, this invention provides a polypeptide having morphogenesis-accelerating activity, said polypeptide defined by the amino acid sequence (I) as described below (SEQ ID No. 1 in the Sequence Listing) which may, in certain cases, be referred to as "polypeptide (I)" in the present specification:

Met Arg Asp Arg Leu Pro Asp Leu Thr Ala Cys Arg Lys Asn
    Asp Asp Gly Asp Thr Val Val Val Val Glu Lys Asp His Phe
    Met Asp Asp Phe Phe His Gln Val Glu Glu Ile Arg Asn
    Ser Ile Asp Lys Ile Thr Gln Tyr Val Glu Glu Val Lys Lys
    Asn His Ser Ile Ile Leu Ser Ala Pro Asn Pro Glu Gly Lys
    Ile Lys Glu Glu Leu Glu Asp Leu Asn Lys Glu Ile Lys Lys
    Thr Ala Asn Lys Ile Arg Ala Lys Leu Lys Ala Ile Glu Gln
    Ser Phe Asp Gln Asp Glu.

Also, the invention provides a polypeptide having morphogenesis-accelerating activity, said polypeptide defined by the amino acid sequence (II) as described below (SEQ ID No. 2 in the Sequence Listing) which may, in certain cases, be referred to as "polypeptide (II)" in the present specification:

Met Arg Asp Arg Leu Pro Asp Leu Thr Ala Cys Arg Thr Asn
    Asp Asp Gly Asp Thr Ala Val Val Ile Val Glu Lys Asp His
    Phe Met Asp Gly Phe Phe His Gln Val Glu Glu Ile Arg Ser
    Ser Ile Ala Arg Ile Ala Gln His Val Glu Asp Val Lys Lys
    Asn His Ser Ile Ile Leu Ser Ala Pro Asn Pro Glu Gly Lys
    Ile Lys Glu Glu Leu Glu Asp Leu Asn Lys Glu Ile Lys Lys
    Thr Ala Asn Arg Ile Arg Gly Lys Leu Lys Ser Ile Glu Gln
    Ser Cys Asp Gln Asp Glu.

Further, the invention also provides the following: a polypeptide characterized by the substitution, addition, and/or deletion of one or more amino acids in the amino acid sequence (I), or the amino acid sequence (II); each above-mentioned polypeptide having substantially the same morphogenesis-accelerating activity as native epimorphins; and each above-mentioned polypeptide further having cell propagation-accelerating activity. As used herein, "the substitution, addition, and deletion of amino acid(s)" can be carried out by the method that is referred to as "site-directed mutagenesis," for example.

According to another embodiment of this invention, there is provided a medicament containing the above-mentioned polypeptide as an effective ingredient. As preferred embodiments of this medicament, there is provided a medicament for use in the prevention and/or treatment of a disease resulting from little expression morphogenetic factors or a disease involving the of destruction of tissue or organ, as well as a medicament for use as a hair growth-promoting agent. In addition to these, there are provided a method for the treatment and/or prevention of a disease resulting from little expression of morphogenetic factors or a disease involving the destruction of tissue or organ, which contains the step of administering the polypeptide to a mammal, including human; a method for diagnosing a disease resulting from little expression of epimorphin, which contains the step of administering the polypeptide to a mammal, including human; and a method for promoting the growth of hair, which contains the step of administering the polypeptide to a mammal, including human.

According to a further embodiment of this invention, there is provided an antibody, preferably a monoclonal antibody, that specifically recognizes the above-mentioned polypeptides. As preferred embodiments of the antibody, there is provided an antibody that specifically binds to the polypeptides and inhibits the morphogenesis-accelerating activity of the polypeptides against epithelial cells, as well as an antibody that specifically binds to an epimorphin having a coiled coil domains (1) and inhibits the morphogenesis-accelerating activity of the epimorphin against epithelial cells. There is also provided a medicament containing the antibody as an effective ingredient, preferably a medicament useful in the prevention and/or treatment of a disease resulting from the excessive expression of epimorphin, as well as a medicament for use as a hair growth-promoting agent. In addition to these, there are provided a method for the treatment and/or prevention of a disease resulting from the excessive expression of epimorphin, which contains the step of administering the antibody to a mammal, including human; a method for diagnosing a disease resulting from the excessive expression of epimorphin, which contains the step of administering the antibody to a mammal, including human; and a method for inhibiting the growth of hair, which contains the step of administering the antibody to a mammal, including human.

BEST MODE FOR CARRYING OUT THE INVENTION

Figure 1:
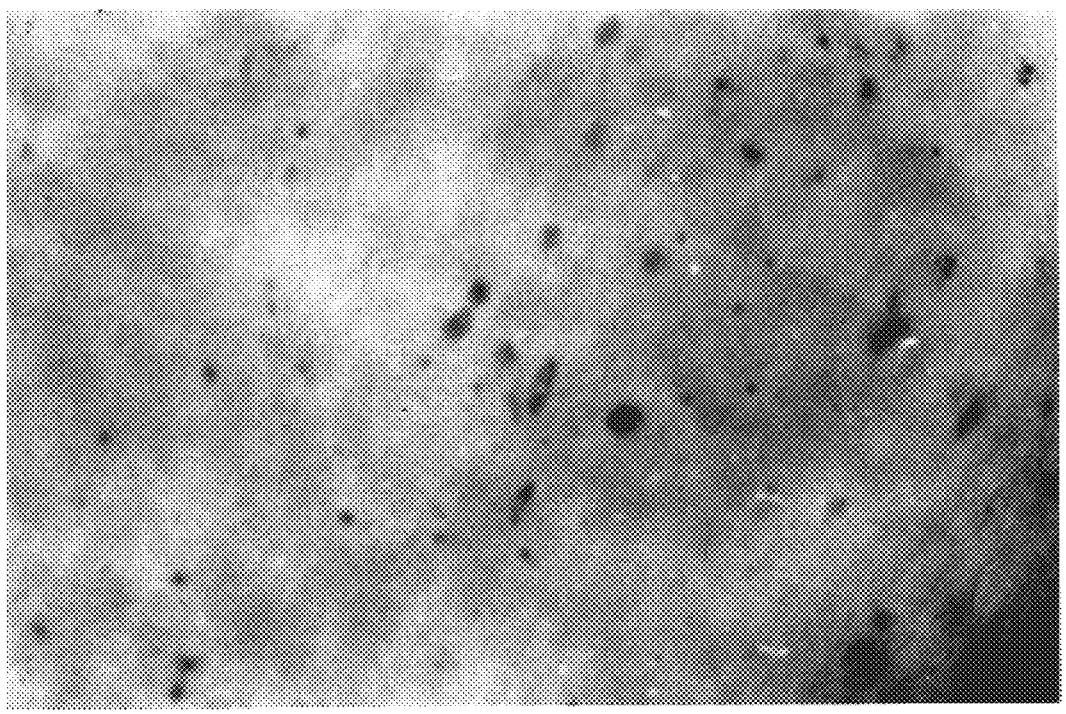
FIG. 1 is a photograph, taken under a microscope, of the morphology of the cells obtained by culturing MDCKII cells (cell strain derived from kidney) in a DH-medium only, which served as the control in the test of Example 2.

Above-mentioned polypeptide (I) provided by this invention corresponds to a coiled coil domain (1) defined by the 1st to 103rd amino acids of human epimorphin (European Patent Application Publn. No. 0698666 ). Above-mentioned polypeptide (II) corresponds to a coiled coil domain (1) defined by the 1st to 104th amino acids of murine epimorphin (European Patent Application Publn. No. 0698666 vide supra). These polypeptides are characterized in that they are excellent in water-solubility as compared to native epimorphins and are soluble in aqueous media such as distilled water, physiological saline solution, or phosphoric acid buffered physiological saline solution. For example, when these polypeptides are dissolved in aqueous media and centrifuged at 100,000×g for 1–2 h, no substantial formation of precipitates is observed if their concentrations are 0.2 mg/ml or less. Nevertheless, the term "water-soluble" as used in the present specification should not be construed as being limited to the above-mentioned specific solubility.

The polypeptides (I) and (II) are characterized in that they possess substantially the same activity as the morphogenesis-accelerating activity of the native epimorphin against epithelial cells. By "the native epimorphin" is meant, for example, an epimorphin biosynthesized by the mesenchyme cells of a mammal. Examples of the native epimorphin are epimorphins derived from human, monkey, cattle, horse, sheep, dog, cat, rabbit, rat and mouse, preferably that derived from human.

Sometimes a plurality of isoforms may exist for the native epimorphin because of its gene splicing. For example, with respect to human epimorphin, there exist human epimorphin comprising 288 amino acids and isoforms A and B of the human epimorphin comprising 287 amino acids and 277 amino acids, respectively; with respect to murine epimorphin, there exist murine epimorphin comprising 289 amino acids and isoforms A and B of the murine epimorphin comprising 288 amino acids and 279 amino acids, respectively. Where the native epimorphin is referred to in the present specification, it is used as a concept encompassing all these isoforms.

The polypeptides of this invention encompass, in addition to the above-mentioned polypeptides (I) and (II), amino acid variants of the polypeptides (I) and (II) wherein one or more amino acids from their constitutive amino acids are substituted with other amino acid(s) or are deleted, and/or one or more arbitrary amino acids are attached to the chains of the polypeptides, said variants being polypeptides substantially having morphogenesis-accelerating activity or cell-proliferating activity against epithelial cells. The kind of one or more amino acids to substitute and/or to be attached is not particularly limited, but it is preferably L-amino acids.

The polypeptides of the invention encompass polypeptides containing the polypeptide (I) or (II) or amino acid variants thereof, as their partial sequences and substantially having morphogenesis-accelerating activity or cell-proliferating activity. For example, one or more amino acids may be bound to the N- or C-terminal of the polypeptide (I) or (II), and preferably any oligopeptide comprising two or more arbitrary amino acids may be bound to. The kind of such amino acid is not particularly limited, but it is preferably selected from L-amino acids. For example, a polypeptide obtained by binding one to ten, preferably five to seven, more preferably six L-histidine (which serves as a tag sequence), to the N-terminal of the polypeptide (I) or (II) is preferred one from the standpoint of production efficiency, because it can be easily purified and detected by using an antibody that specifically binds to the attached tag sequence, or a substance such as nickel. It is also possible that specific tag sequences are attached to the polypeptides for the purpose of improving their functions such as enhanced hydrophilicity or in vivo stability, or of enhancing their morphogenesis-accelerating activity. Besides, fused proteins or the like having improved drug delivery efficiency against certain tissues or organs can be produced by attaching tag sequences capable of binding to specific molecules.

The above-mentioned polypeptides may be in their free forms, but may also be provided as salts of acids such as hydrochlorides, acetates or p-toluenesulfonates, or as their base addition salts such as ammonium salts or organic amine salts. Therefore, where "polypeptide(s)" is referred to in the present specification, it should be construed in the sense that it encompasses the above-mentioned polypeptide in its salt form. Encompassed also within the scope of polypeptides of this invention are those obtained by binding the respective polypeptide with arbitrary carbohydrate (monosaccharide, disaccharide, oligosaccharide, and polysaccharide), those bound to lipids, and further those phosphorylated.

In the examples of the present specification, testing methods for the morphogenesis-accelerating activity against MDCKII cells derived from kidney will be concretely explained with respect to the polypeptide (I) which is a preferred embodiment of the above-mentioned water-soluble polypeptide. Thus, those skilled in the art can readily ascertain that each peptide defined above possesses the desired morphogenesis-accelerating activity, while referring to these examples, or appropriate alternations or modifications further in addition to these methods. Furthermore, since the examples of Japanese Unexamined Application Publn. Hei 6-25,295, for example, also describe the morphogenesis-accelerating activity of epimorphin against epithelial tissues in detail, the application of such a testing system makes it possible to ascertain the morphogenesis-accelerating activity.

In the native human epimorphin, the cell adhesive domain existing in the central fragment (the functional domain: a fragment defined by the 104th to 187th amino acid residues from the N-terminal) is fixed to the surfaces of epithelial cells by being bound to epimorphin receptors existing on the outer cellular surfaces of the epithelial cells; and at the same time, the domain containing the polypeptide (I) (the coiled coil domain of the native human epimorphin: a portion comprising the N-terminal to 103rd amino acid residues of the epimorphin) binds to or acts on the receptors which are participating in the morphogenesis, thus manifesting its morphogenesis-accelerating activity. Not necessarily being adhered to any specified theory, such is a possibility.

Furthermore, the polypeptides of this invention have substantially the same morphogenesis-accelerating activity against epithelial tissues as does the native epimorphin, but the magnitude of their activity is not particularly limited. For example, it is preferred that they can exert the morphogenesis-accelerating activity at the same levels of concentration or less as that of the human native epimorphin. Although the representative testing method for the morphogenesis-accelerating activity (the testing method for tubular structure forming activity against kidney-derived cells) will be concretely described in the examples of the present specification, the morphogenesis-accelerating activity of the polypeptides is not limited to said activity. The polypeptides of this invention also possess strong cell proliferation accelerating activity against epithelial cells. Therefore, the morphogenesis attained by the polypeptides of the invention is characterized in that it is accompanied by the proliferation of cells (increase in the cell number). A test example on cell proliferation accelerating activity by the polypeptides of the invention will be described in the examples of the present specification, but the cell proliferation accelerating activity of the polypeptides of the invention is not to be limited to the specific activity demonstrated by this test example.

Although several kinds of morphogenesis-accelerating activity have been reported for the native epimorphin, it should be understood that they could possibly be part of diverse morphogenesis-accelerating activities exerted by the native epimorphin. Therefore, the term "morphogenesis-accelerating activity" is not limited to the morphogenesis-accelerating activity that has been reported or confirmed in the past, and it needs to be more broadly interpreted. In addition, the notions such as morphogenesis-inducing activity and organ morphogenesis-assisting activity are, for example, a concept embraced by the morphogenesis-accelerating activity. Further, the term "substantially the same" should not be interpreted restrictively. Where the polypeptides of this invention possess, in addition to the morphogenesis-accelerating activity of the native epimorphin, other morphogenesis activitys different therefrom, they are contained in the scope of the invention.

The above-mentioned polypeptides can be synthesized by chemical techniques such as the solid phase method and the liquid phase method, which are conventionally used in peptide synthesis. For protecting groups of amino groups and others as well as condensing agents for condensation reaction in the peptide synthesis, those that can be used are, for example, described in *Protein Engineering Basics and Application;* Suzuki, K., Ed.; Maruzen Co. Ltd.: 1992, Bondansky et al. In *Peptide Synthesis;* John Wiley & Sons: New York, 1976, and Stewart et al. In Solid Phase *Peptide Synthesis;* W. H. Freeman and Co.: San Francisco, 1969. A variety of peptide synthesizers that are commercially available can be utilized in the solid phase method. Moreover, recombinant vectors containing DNA sequences encoding the above-mentioned polypeptides are produced according to biological techniques such as ordinary gene expression manipulations; and then, microorganisms (transformants) transformed with said vectors are prepared and the above-mentioned desired water-soluble polypeptides can be separated from the culture products of said transformants and can be purified. However, the methods of production of the water-soluble polypeptides are not to be limited to these chemical and biological methods.

The base sequence described below may be mentioned as DNA that can be utilized in the production methods through gene expression:

ATG CGG GAC CGG CTG CCA GAC CTG ACG GCG
  TGT AGG AAG AAT GAT GAT GGA GAC ACA GTT
  GTT GTG GTT GAG AAA GAT CAT TTC ATG GAT
  GAT TTC TTC CAT CAG GTG GAG GAG ATT AGA
  AAC AGT ATT GAT AAA ATA ACT CAA TAT GTT
  GAA GAA GTA AAG AAA AAC CAC AGC ATC ATT
  CTT TCT GCA CCA AAC CCG GAA GGA AAA ATA
  AAA GAA GAG CTT GAA GAT CTG AAC AAA GAA
  ATC AAG AAA ACT GCG AAT AAA ATT CGA GCC
  AAG TTA AAG GCT ATT GAA CAA AGT TTT GAT
  CAG GAT GAG (SEQ ID NO.3).

wherein only the sense chain is shown with the abbreviation of the complementary base sequence, and the initiation point is 5'-end and the termination point is 3'-end.

This DNA corresponds to the 1st to 309th nucleotides within DNA encoding the full-length native human epimorphin (the nucleic acid sequence set forth in formula (6) as disclosed in Japanese Unexamined Patent Application Publn. Hei 6-25,295) and is DNA encoding the above-mentioned polypeptide (I). Production of the polypeptide (II) can employ, for example, the DNA defined by the 1st to 312th nucleotides within DNA encoding the full-length native murine epimorphin (the nucleic acid sequence set forth in formula (12) as disclosed in Japanese Unexamined Patent Application Publn. Hei 6-25,295).

Further, it is possible to easily produce the amino acid variants by standard methods using above-mentioned the human- or mouse-derived DNA. Such methods can, for example, utilize the recombinant PCR technique as described in *PCR Protocols;* HJB Publisher: 1991; pp 155–160, or the preparation method of mutated genes using PCR as described in *Experimental Medicine;* Supplement Vol. 8, No. 9; Yodo Co. Ltd.: 1990; pp 63–67. Methods of gene expression that can be utilized to produce the desired polypeptides may, for example, employ the technique fully described in the examples of the specification of European Patent Application Publn. No. 0698666, but they are not to be limited thereto.

The above-mentioned polypeptides of this invention possess an activity for accelerating the morphogenesis of epithelial tissues or organs by acting on the epithelial cells. Accordingly, the polypeptides of the invention are useful as the effective ingredient of a medicament for the treatment and/or prevention of a disease involving the aberration of the morphogenesis of tissue or organ or a disease involving the destruction of tissue or organ each of which results from endogenous morphogenetic factors, or are useful as the effective ingredient of a medicament for the diagnosis of the above-mentioned diseases. The polypeptides are also useful as the effective ingredient of a medicament to be used for a hair growth-promoting agent. The term "medicament(s)" in the present specification is used in the broadest sense, which includes those for use in the prevention, treatment, or diagnosis of diseases of mammals including human in addition to hair growth-promoting agents and hair growth inhibitors that are normally classified into "quasidrugs."

A variety of morphogenetic factors, including native epimorphins, is known. The medicaments of this invention are useful in the prevention and/or treatment of diseases involving the aberration of the morphogenesis of tissue or organ that results from the morphogenetic factors, especially epimorphin. Furthermore, the medicaments of this invention can be applied for the purpose of accelerating the regeneration of epithelial tissues or organs against diseases (as used herein, including injury) involving the destruction of the epithelial tissues or organs such as inflammatory disorders, carcinoma, burn, operations, or wound, as well as their healing processes. More specifically, it is suggested that other physiologically active substances having morphogenesis-accelerating activity (e.g., HGF and EGF) can treat diseases such as the following: a renal disorder such as chronic nephritis; chronic and acute pulmonary diseases such as pneumonia, pulmonary emphysema, pulmonary tuberculosis, chronic obstructive pulmonary disease, pneumoconiosis, and aspiration pneumonia; tracheal and bronchial diseases such as chronic bronchitis; hepatic disorders such as acute hepatitis, chronic hepatitis, cirrhosis, and fulminant hepatitis; carcinoma; benign prostatic hyperplasia; peptic ulcer; wound; and cutaneous ulcer. It is therefore expected that the medicaments of this invention are effective for these diseases.

Furthermore, when the medicaments of this invention are administered to patients suffering from diseases that result from little expression of epimorphin, generally the alleviation of symptoms of said diseases is noted; and thus, the conclusive diagnosis of the diseases is enabled. As is specifically shown in the examples of the present specification, the polypeptides of the invention possess strong cell-proliferating and morphogenesis-accelerating activity particularly against renal cells. Therefore, the medicaments of the invention can most preferably be used against kidney diseases requiring the regeneration or protection of renal tissues such as the epithelial cells of uridiferous tubule at the time of their treatment. For example, the medicaments of the invention can be applied to kidney diseases such as chronic nephritis (e.g., acute glomerular nephritis, rapidly progressive nephritis, or chronic glomerular nephritis), nephritic syndrome, chronic renal insufficiency, and renal carcinoma.

The subjects to which the medicaments of this invention are applied are not limited to the diseases illustrated above, and it should be understood that they are applicable to diseases for which one or more morphogenetic factors, especially that of epimorphin, is supposedly responsible, and to diseases involving the substantial destruction of tissue and organ. In addition, the utility of a hair growth-promoting agent that contains the polypeptide of the invention as the effective ingredient should be interpreted in the broadest sense, including hair growth promotion and trichogenous promotion.

One or more kinds of substance selected from the above-mentioned polypeptides may be used for a medicament of this invention as such; however it is preferred to prepare a medicinal composition containing one or more kinds of the substance as the effective ingredient together with one or more kinds of pharmaceutically acceptable additives for formulation purposes,and to use the medicinal composition for the treatment and/or prevention of the above-mentioned diseases. From the standpoint of in vivo kinetics such as solubility, absorption and excretion, and/or production methods, the above-mentioned polypeptides may be in the form of physiologically acceptable salts. As for the routes of administration of the medicinal compositions systemic administration such as intravenous, rectal, and oral one and, in addition, local administration such as external application, through eye drop, nasal drop, or ear drop, and local injection can be mentioned.

The preferred forms of medicinal compositions of this invention are, for example, agents for systemic administration such as injectables or drips for intravenous administration and agents for local administration such as ointments, creams, patches and local injectables. In certain cases, medical compositions having their effective ingredients included in liposome or the like and those bound to antibodies or the like may be used to possibly improve their affinity and selectivity against targeted organs. It is, however, needless to mention that the administration routes can appropriately be chosen depending on the type of disease to be the subject of application, the purposes of treatment or prevention, the type of the affected part, the conditions of patients and that dosage forms suitable for the respective routes of administration can adequately be chosen also. The forms in cases where they are used for diagnostic agents are not particularly limited. The methods of diagnosis encompass the cases where the viable samples separated and collected from patients are used, in addition to those where the medicaments of this invention are administered to patients.

Further, the hair growth-promoting agent containing as the effective ingredient, one or more kinds of the above-mentioned polypeptides may preferably be provided as the dosage form suited to the purpose of use which is a hair growth-promoting agent, such as a cream, a nebula, a solution for application, or a patch. The above-mentioned water-soluble polypeptides may be in the form of physiologically acceptable salts; and preferably, suitable surfactants or liposoluble substances may also be compounded into the creams or the like so that the water-soluble polypeptides which are the effective ingredients can effectively be absorbed transdermally through cutaneous keratin layers. Furthermore, the utility of the polypeptides of this invention is not limited to the above-mentioned medicaments and they can be used as additives for cell culture media.

According to the second embodiment of this invention, there is provided an antibody, preferably a monoclonal antibody, that specifically recognizes the polypeptide of this invention (preferably, the above-mentioned polypeptide (I) or (II)). The antibodies of the invention can specifically bind to the polypeptides of the invention (preferably the above mentioned peptides (I) and (II)) or to epimorphin like factors having the coiled coil domain (1) (preferably the native epimorphin derived from human or mouse), and they have an inhibitory function against the morphogenesis-accelerating activity of those substances against epithelial cells. The term "an epimorphin like factors" as used in the present specification is a concept encompassing native epimorphins, modified forms thereof that possess substantially the same physiological activitys as do the native epimorphins (modified epimorphin), and mutants thereof having amino acid mutation that have substantially the same physiological activitys as do the native epimorphins.

In the present specification, "modified epimorphin" means a polypeptide having substantially the same physiological activitys as does the native epimorphin (e.g., cell adhesion activity against epithelial cells and morphogenesis-accelerating activity against epithelial cells); and it means either of the following: a polypeptide being a partial polypeptide sequence that is derived from a polypeptide sequence of the native epimorphin (normally a polypeptide comprising from 277 to 289 amino acids) and a polypeptide containing the partial polypeptide sequence derived from the polypeptide sequence of the native epimorphin. For example, the polypeptide obtained by deletion of the hydrophobic domain at the C-terminal of the native epimorphin (Japanese Unexamined Patent Application Publn. Hei 6-25, 295) is a representative compound of the modified epimorphin. Further, in the present specification "mutants having amino acid mutation (hereinafter "mutants") of native epimorphin or modified epimorphin" means a polypeptide having substantially the same above-mentioned physiological activities as does the native epimorphin; and in the native epimorphin or the modified epimorphin, one or more amino acids among the amino acids constituting a polypeptide chain thereof are substituted with other amino acids or are deleted, and/or one or more arbitrary amino acids are inserted into the polypeptide chain, thus leading to said polypeptide.

It should be understood that aside from the modified epimorphins such as those disclosed in the above-mentioned patent publications and others, modified epimorphins that can be produced according to the disclosed methods or their modified (including chemically modified) versions are encompassed by the modified epimorphin as used in the present specification insofar as they satisfy the above definitions. Further, methods for the production of the amino acid variants of a native epimorphin or an modified epimorphin are concretely explained in the specifications of Japanese Patent Application Nos. Hei 7-175,539 and Hei 8-99,684. However, they should not be limited to these methods and may be the amino acid variants produced by any methods. Furthermore, methods for assaying physiological activities of those modified epimorphins and their amino acid variants can be carried out following, with modification if necessary, the method for assaying physiological activities of the native epimorphins as fully explained in Japanese Patent Application Publn. No. Hei 6-25295 or in International Publn. WO97/40158. For example, the morphogenesis-accelerating activity against murine fetal bronchus or the morphogenesis-accelerating activity against murine fetal maxillary cutis, as described in the examples of specification of Japanese Patent Application No. Hei 8-102553, may be ascertained.

In the past, MC-1 has been known for an antibody that binds to epimorphins and inhibits their activitys. (Japanese Patent Application Publn. Hei 6-25295; Cell 69, 471–481 (1992).) The antibodies of this invention, similarly to MC-1, are useful in the elucidation of mechanism of the normal morphogenesis of epithelial tissues by epimorphin like factors; they can also be used in the elucidation of the crisis mechanism of diseases resulting from the abnormal expression (excessive expression) of native epimorphins as well as can be used for the effective ingredients of medicaments beneficial to the prevention and/or treatment of these diseases. Further, the antibodies of the invention are useful as the effective ingredients of medicaments that are used as hair growth inhibitors.

As an example of the production method for the antibodies of this invention, the method for producing a polyclonal antibody by the use of the above-mentioned polypeptide (II) has been fully described in the examples. Thus those skilled in the art will readily understand the following: the polypeptides of this invention can act as antigens against mammals under suitable conditions; they can immunize the mammals according to standard methods; and polyclonal antibodies or monoclonal antibodies that specifically recognize arbitrary polypeptides encompassed by the polypeptides of the invention can be easily produced according to well-known and conventional methods.

Examples of the diseases that result from the excessive expression of one or more factors among the morphogenetic factors are chronic articular rheumatism, cancers such as renal cell carcinoma and carcinoma cutaneum, arteriosclerosis, collagen disease, hematopoietic organ disorder, renal disorder, muscular dystrophy, osteoporosis, neurofibromatosis, Sturge-Weber syndrome, nodular sclerosis, dysraphism, abnormal segmentation, vagus nerve disorder, callosal genesis, encephalo foramen disease and hydrocephalus. The medicaments containing the antibodies of this invention as effective ingredients can be expected to be useful in the treatment and/or prevention of these diseases as well as their diagnosis.

Nevertheless, it should be understood that the subjects of application of the medicaments of the invention are not limited to those diseases and can rather be all diseases for which the excessive expression of one or more morphogenetic factors, especially that of native epimorphins, is supposedly responsible. Further, the utility of hair growth inhibitors containing the above-mentioned antibodies as effective ingredients is to be interpreted in the broadest sense, including epilation, hair growth inhibition, and trichogenous inhibition. Moreover, the medicaments containing the antibodies of the invention as effective ingredients are normally prepared as medicinal compositions by using one or more additives for formulation purposes which are pharmaceutically acceptable, and what has been explained above may be applicable to, among others, the forms, the preparation methods, and the routes of administration with regard to the medicinal compositions.

EXAMPLES

Although this invention will be explained in more detail hereinbelow, the scope of the invention is not to be limited to the examples that follow.

Example 1

Production of Polypeptide of the Invention

PCR was conducted to prepare cDNA: ATGCATCAT-CATCATCATCAT (SEQ ID NO:4) encoding methionine and six histidines was attached to the 5'-side of a DNA sequence encoding the 1st to 104th amino acids from the N-terminal of the native epimorphin derived from mouse (DNA defined by the 1st to 312th nucleotides of the nucleic acid sequence set forth by formula (12) which was disclosed in Japanese Patent Application Publn. Hei 6-25,295) and a stop codon was attached to the 3'-end thereof to form the DNA which encodes a total of 111 amino acids. Said cDNA was incorporated into NdeI and NheII sites of a pET3C vector the domain between two EcoRV sites of which was deleted, and an expression vector was prepared.

According to the Hanahan method (*Laboratory Manual Genetic Engineering:* published by Maruzen Co.), the resulting vector was introduced to an *E. coli* BL21 strain that had been made into competent cells. The introduction method was carried out as follows: the competent cells were dissolved on ice; the vector was added to 100 μl of the solution in the appropriate amount (1 μl of DNA solution, of which concentration was 1 mg/ml); it was allowed to stand on ice for 30 min; subsequently, the solution was allowed to stand in an incubator at 42° C. for 2 min; and finally it was allowed to stand on ice for 30 min to accomplish the introduction.

Next, the above-mentioned transformants were inoculated to a LB plate(1% Bacto-tryptone, 0.5% Bacto-yeast extract, 1% NaCl, and 1.5% Bacto-agar) containing ampicillin (50 μg/ml), and grown colonies were selected and the first screening of the transformants was performed. Further, in order to finally confirm transformants having the expression vector, the presence or absence of DNA encoding the desired polypeptide was determined by PCR, at which point the DNA was retained in nine clones out of ten; thus, transformants having the expression vector were obtained. The resulting transformant was grown in a large quantity by shake culture at 37° C. using a liquid LB medium (1% Bacto-tryptone, 0.5% Bacto-yeast extract, and 1% NaCl) containing ampicillin (50 μg/ml); and then, IPTG, which is a substance for expression induction, was added to the medium so that its final concentration could be 1 mM. Subsequently, shake culture continued at 37° C. for 2 h and the desired polypeptide was expressed in *E. coli*. Purification of the expressed polypeptide was carried out using a $Ni^{2+}$-NTA-Argarose (manufactured by QIAGEN Cat. No. 30,230) according to the protocol as attached thereto. SDS- PAGE (CBB staining) confirmed that the purified polypeptide had a purity of not less than 95%. The solubility of the polypeptide after purification against phosphate buffered saline solution (PBS) was 0.15 mg/ml.

Example 2
Morphogenesis-Accelerating Activity of Polypeptide of the Invention Against MDCKII Cells (Strain Derived from Kidney)

The organ morphogenesis-accelerating activity of the polypeptide prepared in Example 1 was evaluated in the following manner.

A sterilized tref tube was erected in ice. To the tref tube were added a 1/10-volume portion of a 10×DH-medium (mixed medium of equal amounts of Dalbeco-modified MEM medium and Ham F12 medium) and a 1/10-volume portion of a reconstitution buffer (260 mM $NaHCO_3$, 200 mM HEPES, and 50 mM NaOH). Further, an 8/10-volume portion of collagen solution I-P (available from Nitta Gelatin) was added inside the tref tube and it was mixed by pipetting. After the polypeptide prepared in Example 1 was dialyzed against a DH-medium, it was added to the tref tube so that its final concentration was 15 µg/ml. An equal amount of DH-medium was added as a control. Subsequently, MDCKII cells, a strain derived from kidney, were added to the tref tube and mixed by pipetting.

To 48 wells of a multi-well dish was added 200 µl/well of the above mixture, and the mixture was gelled by being maintained in an incubator at 37° C. for 1 h. Serum-free DH medium was added at 800 µl/well and equilibration was effected at 37° C. for 1 h, and then, the medium was carefully removed so as not to damage the gel. Subsequently, a serum-free DH medium was added at 500 µl/well, and morphological observation was made by culturing the medium in a 5% carbon dioxide incubator at 37° C. for 1–2 weeks.

Figure 2:
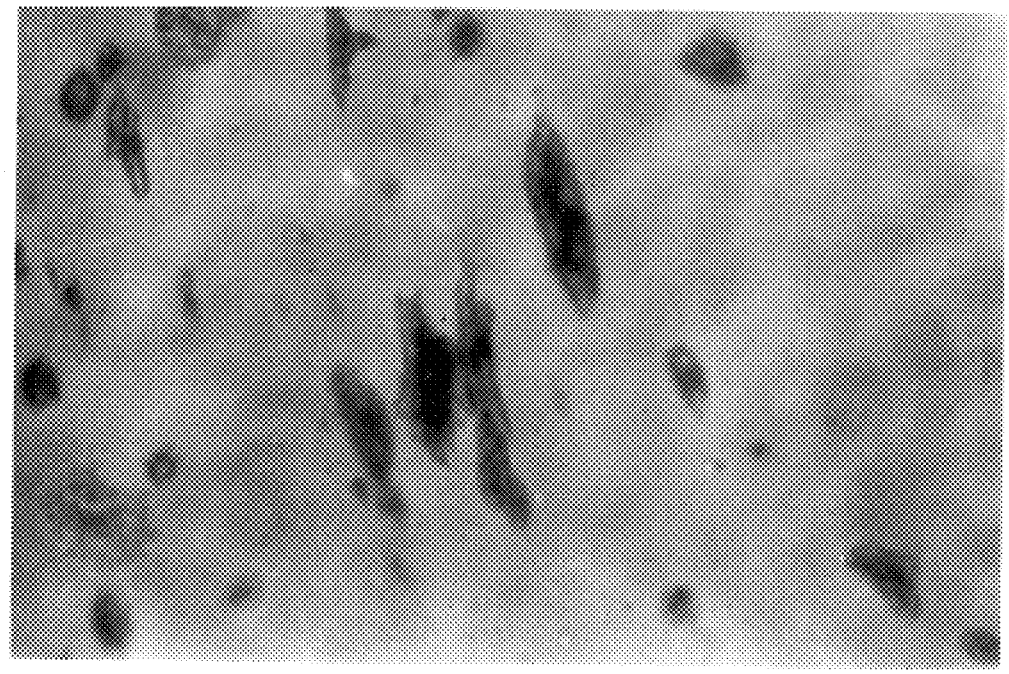
FIG. 2 is a photograph, taken under a microscope, of the morphology of the cells obtained by culturing MDCKII cells (cell strain derived from kidney) in the presence of a polypeptide according to this invention (15 µg/ml), as well as the morphology of the tube like structure derived from said cells.
Figure 3:
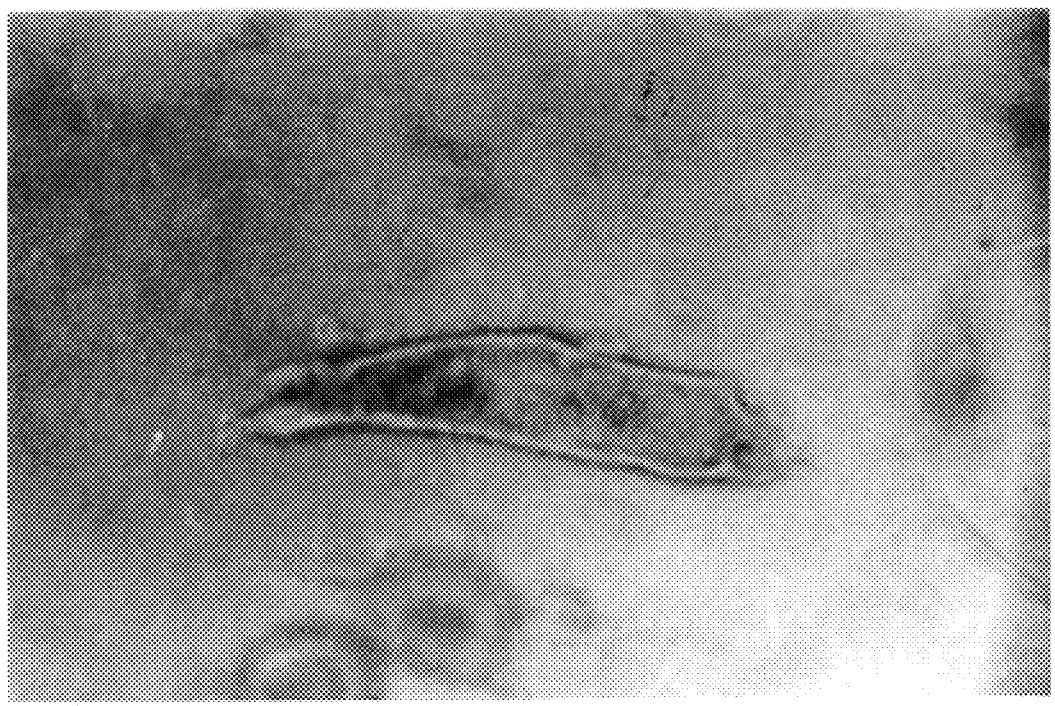
FIG. 3 is a photograph, taken under a microscope, of the morphology of the cells obtained by culturing MDCKII cells (cell strain derived from kidney) in the presence of the polypeptide according to the invention (15 µg/ml), as well as the morphology of the tissue derived from said cells at a higher magnification than those in the cases of FIGS. 1 and 2.

FIGS. 1–3 are photographs showing the results of photographing the cells and the tissue generated from the cells after two weeks' cultivation. FIG. 1 shows the result of the control (DH-medium only), and FIG. 2 shows the result of cultivation of the gel with addition of the polypeptide of this invention (15 µg/ml). The photographs of FIGS. 1 and 2 show the results of photographing at the same magnifications (40-fold). FIG. 3 shows the result of photographing the culture obtained by addition of the polypeptide of the invention (15 µg/ml) to the gel, at a high magnification (100-fold). When the polypeptide of the invention was added to a collagen gel, the cells (MDCKII) formed tubular structure in a three dimensional manner. This result indicates that the polypeptide of the invention possesses morphogenesis-accelerating activity (organ morphogenesis-assisting activity)

Example 3
Preparation of Polypeptide of the Invention

Similarly to Example 1, a polypeptide of this invention was prepared: a DNA sequence encoding the 1st to 103rd amino acids from the N-terminal of the native epimorphin derived from human (DNA defined by the 1st to 309th nucleotides of the nucleic acid sequence set forth by formula (6) which was disclosed in Japanese Patent Application Publn. Hei 6-25,259) was used in place of the DNA sequence encoding the 1st to 104th amino acids from the N-terminal of the native epimorphin derived from mouse. The same experiment as that in Example 2 was conducted with this polypeptide. It was then confirmed that this peptide possesses organ morphogenesis-accelerating activity against the MDKII cells, the cell strain derived from kidney, similar to that of the polypeptide of Example 1.

Example 4
Preparation of Antibody Specifically Binding to Polypeptide of the Invention and Inhibition of Morphogenesis by Said Antibody Rats were immunized according to the standard method (*Monoclonal Antibody Experimental Manual;* Kodansha Scientific: pp 184–188) with using the polypeptide obtained in Example 1 (hereinafter referred to as "H1") and a polypeptide as the control (hereinafter referred to as "H3"), respectively. Methionine and six histidines were attached to the N-terminal of a partial polypeptide of the native epimorphin derived from mouse that posseses no morphogenesis-accelerating activity (polypeptide defined by the amino acid sequence of from 189th to 263rd amino acids from N-terminal) to form the control polypeptide. Antisera against the respective polypeptides were thus obtained. IgG fractions were purified from each antiserum using a HiTrap Protein G (available from Pharmacia Inc.; code No. 17-0404-01) to produce a polyclonal antibody. The purification manipulations were performed according to the protocol which was attached. After the resulting polyclonal antibodies were subjected to western blotting to check respective specificity, their titers were adjusted for use in the following experiment.

Figure 4:
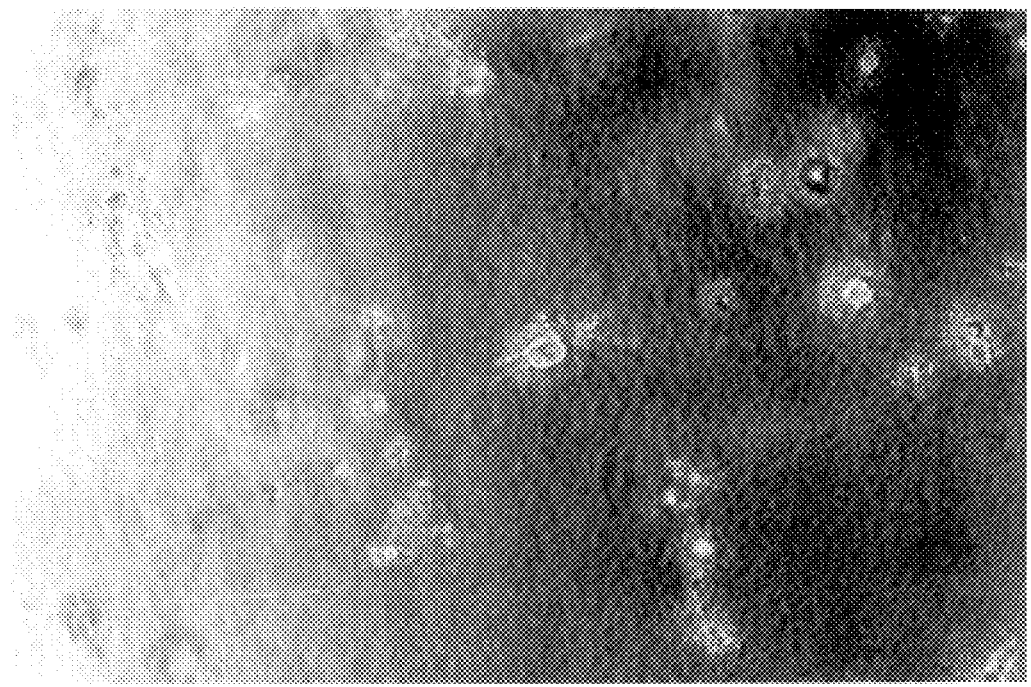
FIG. 4 is a photograph, taken under a microscope, of the morphology of the cells obtained by culturing MDCKII cells (cell strain derived from kidney) in a DH-medium only, which served as the control in the test of Example 4.
Figure 5:
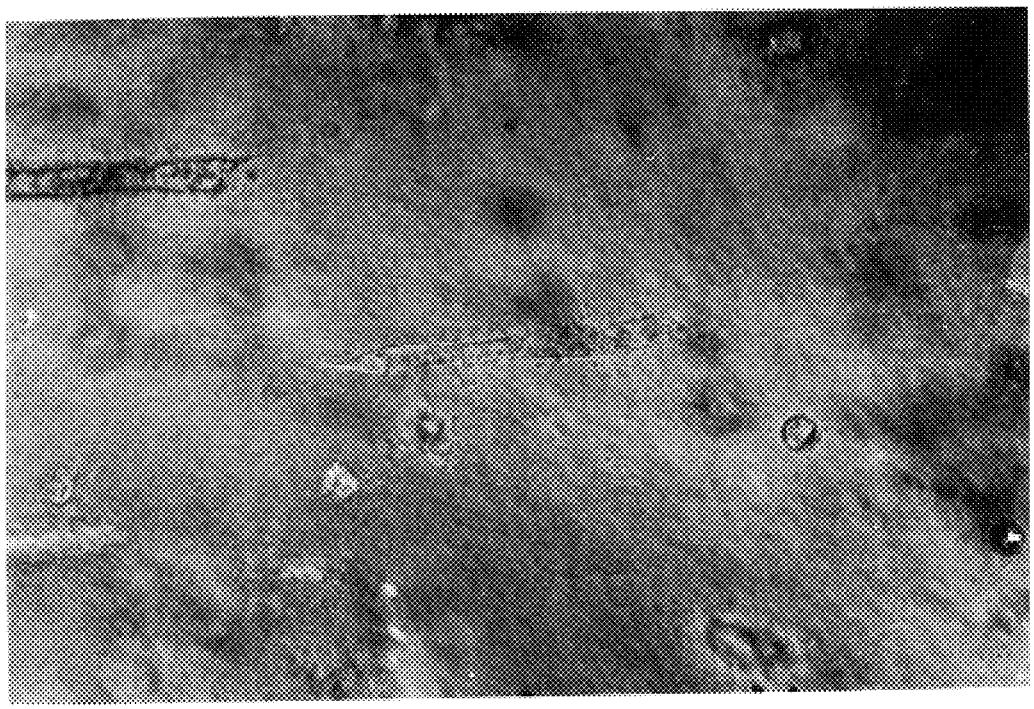
FIG. 5 is a photograph showing the morphology of the cells and the tissue derived from said cells in the case where a polypeptide according to the invention (H1, 3 µg/ml) was added to a gel and MDCKII cells (cell strain derived from kidney) were cultured, which served as the control (positive control) in the test of Example 4.
Figure 6:
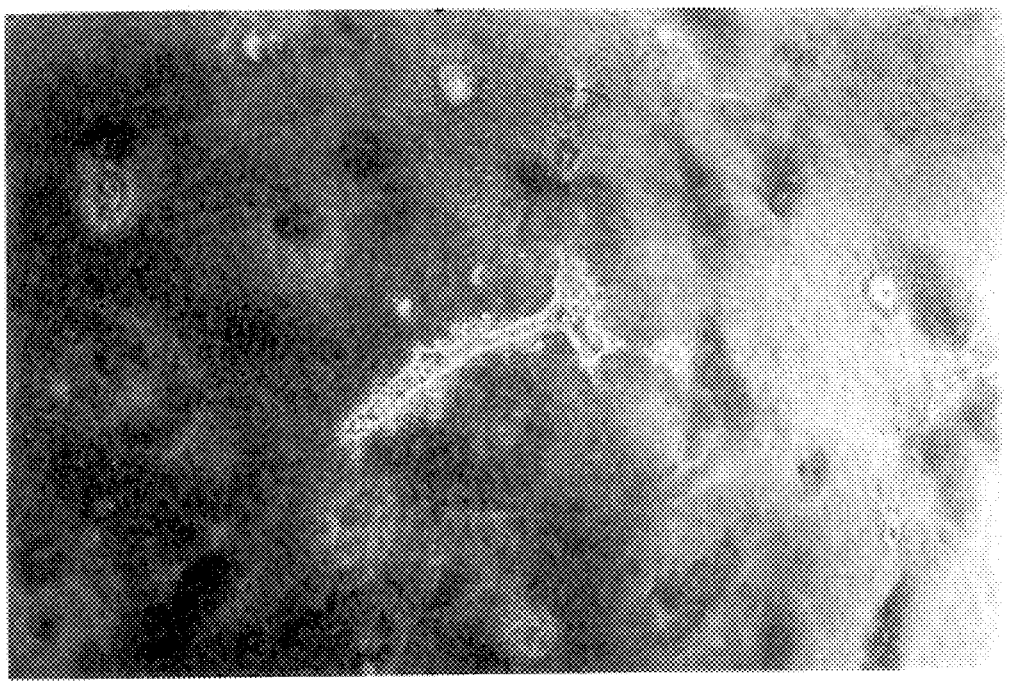
FIG. 6 is a photograph showing the morphology of the cells and the tissue derived from said cells in the case where the polypeptide according to the invention (H1, 3 µg/ml) and the anti-H1 antibody (5.2 µg/ml) were added to a gel and MDCKII cells (cell strain derived from kidney) were cultured.
Figure 7:
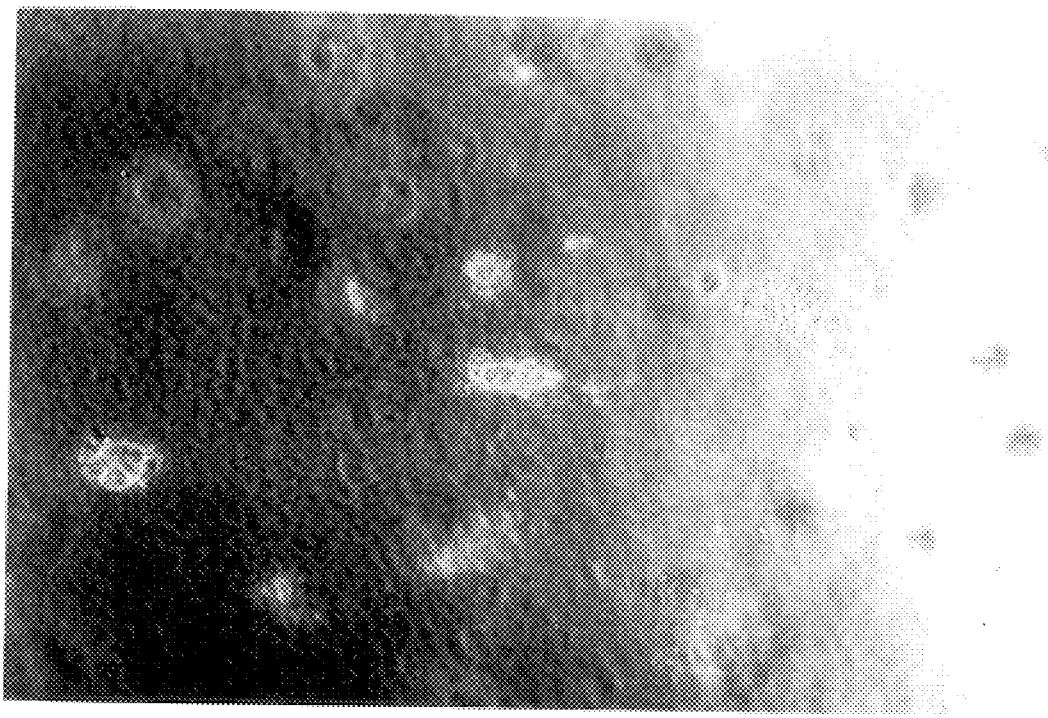
FIG. 7 is a photograph showing the morphology of the cells and the tissue derived from said cells in the case where the polypeptide according to the invention (H1, 3 µg/ml) and the anti-H1 antibody (26 µg/ml) were added to a gel and MDCKII cells (cell strain derived from kidney) were cultured.
Figure 8:
FIG. 8 is a photograph showing the morphology of the cells and the tissue derived from said cells in the case where the polypeptide according to the invention (H1, 3 µg/ml) and the anti-H1 antibody (130 µg/ml) were added to a gel and MDCKII cells (cell strain derived from kidney) were cultured.
Figure 9:
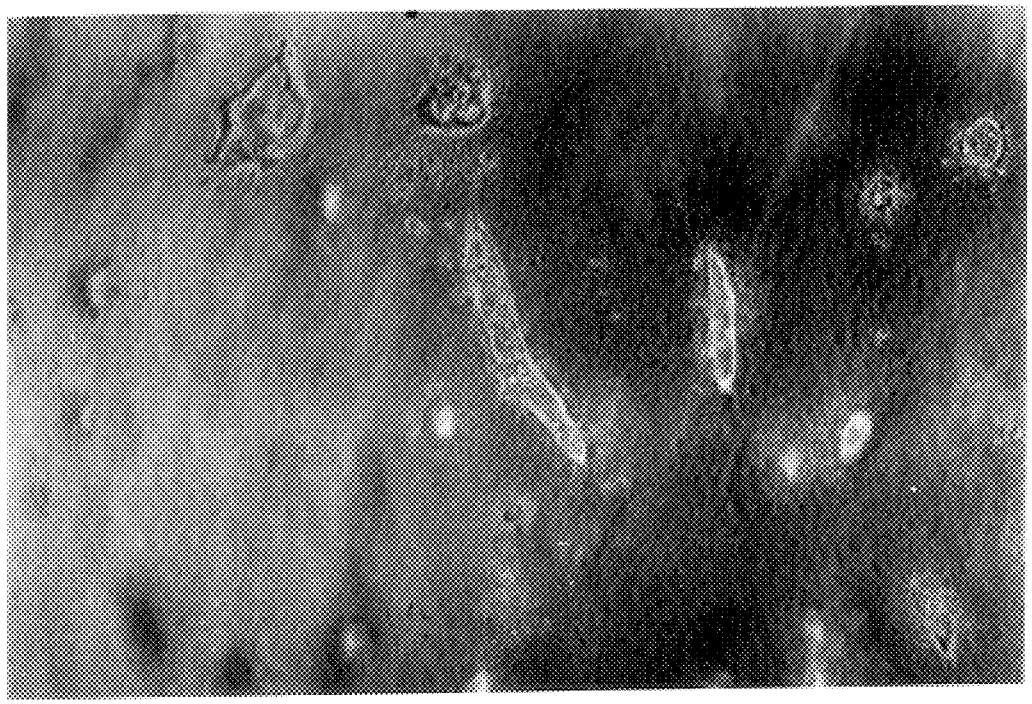
FIG. 9 is a photograph showing the morphology of the cells and the tissue derived from said cells in the case where the polypeptide according to the invention (H1, 3 µg/ml) and the anti-H3 antibody (5.2 µg/ml) were added to a gel and MDCKII cells (cell strain derived from kidney) were cultured.
Figure 10:
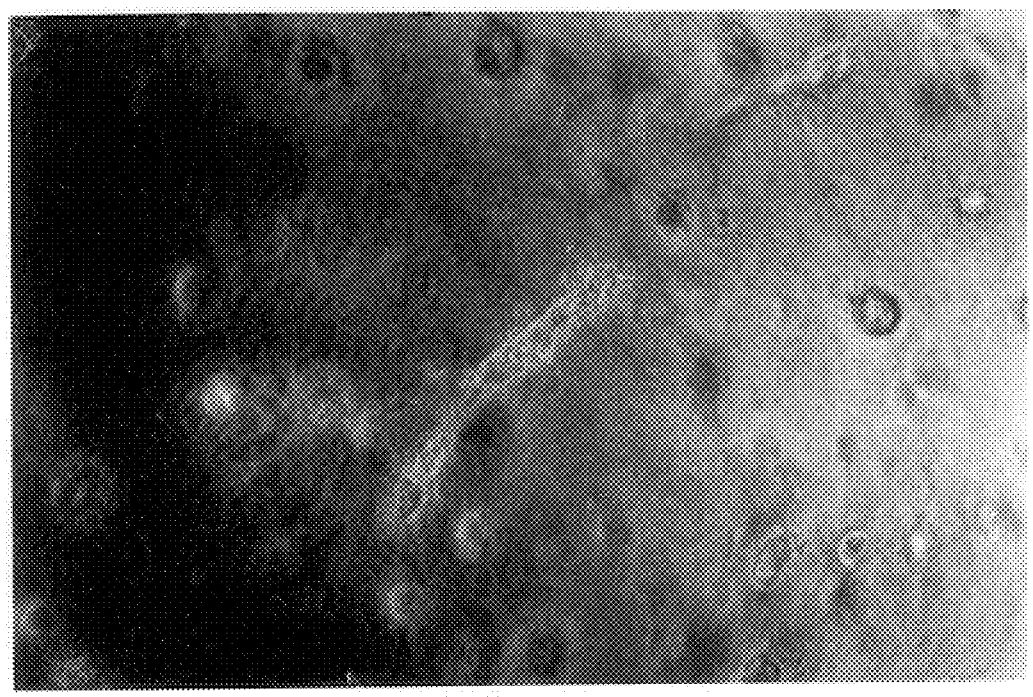
FIG. 10 is a photograph showing the morphology of the cells and the tissue derived from said cells in the case where the polypeptide according to the invention (H1, 3 μg/ml) and the anti-H3 antibody (26 μg/ml) were added to a gel and MDCKII cells (cell strain derived from kidney) were cultured.
Figure 11:
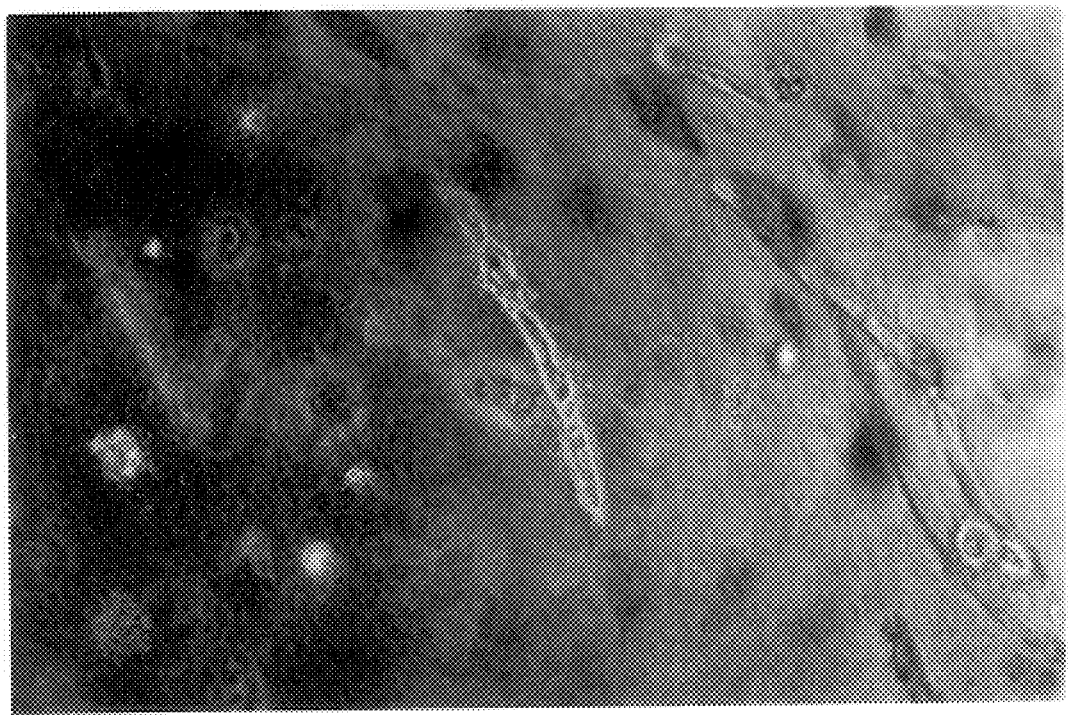
FIG. 11 is a photograph showing the morphology of the cells and the tissue derived from said cells in the case where the polypeptide according to the invention (H1, 3 μg/ml) and the anti-H3 antibody (130 μg/ml) were added to a gel and MDCKII cells (cell strain derived from kidney) were cultured.

Employing the experimental conditions of Example 2 under which tubular structures were formed in the MDCKII cells, the cell strain derived from kidney, by the polypeptide of this invention, each polyclonal antibody was added to a serum-free DH-medium (500 µl/well) immediately before the final incubation. Investigation was then carried out to find the effect of each of the above antibodies influencing on the morphogenesis-accelerating activity of polypeptide of the invention. The results are shown in Table 1 and FIGS. 4 through 11. In the table "++" indicates that morphogenesis has progressed; "+" indicates that the morphogenesis has been inhibited 80%; and "−" indicates that the morphogenesis has been inhibited 100%. FIGS. 4 through 11 are the photographs showing the results of photographing, under a microscope, cells and the tissue generated by the cells on the 11th day of cultivation. FIG. 4 shows the result of the control (DH-medium only) and FIG. 5 shows the result of cultivation with addition of the polypeptide of the invention (H1, 3 µg/ml) into the gel. FIGS. 6, 7, and 8 show the results of cases where the anti-H1 antibody was added at concentrations of 5.2 µg/ml, 26 µg/ml, and 130 µg/ml, respectively, and FIGS. 9, 10, and 11 show the results of cases where the anti-H3 antibody was added at concentrations of 5.2 µg/ml, 26 µg/ml, and 130 µg/ml, respectively. All the photographs were taken at the same magnification (40-fold).

TABLE 1

| antibody | 5.2 µg/ml | 26 µg/ml | 130 µg/ml |
| --- | --- | --- | --- |
| anti-H1 antibody | ++ | ++ | − |
| anti-H3 antibody | ++ | ++ | ++ |

As is apparent from these results, the anti-H1 antibody inhibits the morphogenesis-inducing activity of polypeptide (H1) of this invention against the MDCKII cells in a concentration-dependent manner, whereas the anti-H3 antibody does not have an inhibitory activity to the morphogenesis-inducing activity. This fact has demonstrated that the morphogenesis-accelerating activity observed in the experiment of Example 2 does not originate in, for example, impurities from *E. coli* but depends on the activity of polypeptide (H1) of the invention itself. Further, because the anti-H1 antibody of the invention effectively inhibits the morphogenesis-accelerating activity of the polypeptide H1 similar to that of epimorphin, it has been established that this antibody is useful as a medicament for the treatment and/or prevention of a disease resulting from the excessive expression of epimorphin.

Example 5
Activity of Polypeptide of the Invention Against Cell Propagation

The effect of polypeptide of the invention prepared in Example 1 on cell propagation was evaluated in the following manner. Used as the medium was a serum-free DH medium or a serum-free DH medium into which 0.003–0.15 mg/ml of polypeptide of the invention had been dissolved, and MDCKII cells were inoculated so that 12,000 cells/ml could be attained in a 24-well dish for tissue culture. After cultivation in a 5% carbon dioxide gas incubator at 37° C. for 5 days, the medium was removed and washing with PBS(−) was done twice. The cells were peeled from the well bottom with trypsin-EDTA, and then they were stained with trypan blue to count viable cells. As Table 2 shows, when the MDCKII cells were cultured as monolayer in the serum-free medium, the viable cells decreased to about 1/10 after 5 days if the polypeptide of this invention was not added to the culture solution (control). On the other hand, when the polypeptide of the invention was added to the culture solution, the propagation of the MDCKII cells was induced in the manner depending on the concentration of the added polypeptide of the invention despite its serum-free cultivation. When 0.075 mg/ml of polypeptide of the invention was added to the culture solution, it was confirmed that after 5 days' cultivation viable cells were present more than 10-fold as compared to the start of cultivation. This result is comparable with the effect of addition of a 10% fetal bovine serum, and it has demonstrated that the polypeptide of the invention has very strong cell-proliferating activity.

TABLE 2

| polypeptide concentration (mg/ml) | the number of cell after cultivation |
|---|---|
| 0.15 | 140,000 |
| 0.075 | 140,000 |
| 0.05 | 90,000 |
| 0.0375 | 83,000 |
| 0.03 | 54,000 |
| 0.015 | 14,000 |
| 0.0075 | 9,800 |
| 0.003 | 5,300 |
| 0    (DH-medium) | 1,800 | the number of cell at the start of cultivation: 12,000

Industrial Applicability

The polypeptides of this invention are soluble in aqueous media such as physiological saline solution and have morphogenesis-accelerating activity against epithelial tissues; therefore, they are useful as the effective ingredients of medicaments for the prevention and/or treatment of diseases resulting from the aberration of morphogenesis.

What is claimed is:

1. An isolated polypeptide consisting of the amino acid sequence set forth in SEQ ID NO: 1 in the Sequence Listing.

2. The polypeptide according to claim 1, wherein at least one member selected from the group consisting of sugar, lipid, and a phosphate group has modified amino acid residue(s) of the amino acid sequence.

3. A cell culture medium containing a polypeptide according to claim 1.

4. An isolated polypeptide consisting of the amino acid sequence set forth in SEQ ID NO: 2 in the Sequence Listing.

5. The polypeptide according to claim 4, wherein at least one member selected from the group consisting of sugar, lipid, and a phosphoric acid group binds to amino acid residue(s) of the amino acid sequence.

6. A cell culture medium containing a polypeptide according to claim 4.

* * * * *

SEQUENCE LISTING

<160> NUMBER OF SEQ ID NOS: 4

<210> SEQ ID NO 1
<211> LENGTH: 103
<212> TYPE: PRT
<213> ORGANISM: Homo sapiens

<400> SEQUENCE: 1

Met Arg Asp Arg Leu Pro Asp Leu Thr Ala Cys Arg Lys Asn Asp Asp
 1               5                  10                  15

Gly Asp Thr Val Val Val Glu Lys Asp His Phe Met Asp Asp Phe
                20                  25                  30

Phe His Gln Val Glu Glu Ile Arg Asn Ser Ile Asp Lys Ile Thr Gln
            35                  40                  45

Tyr Val Glu Glu Val Lys Lys Asn His Ser Ile Ile Leu Ser Ala Pro
        50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Ala Lys Leu Lys Ala Ile Glu
                85                  90                  95

Gln Ser Phe Asp Gln Asp Glu
            100

<210> SEQ ID NO 2
<211> LENGTH: 104
<212> TYPE: PRT
<213> ORGANISM: Mouse

<400> SEQUENCE: 2

Met Arg Asp Arg Leu Pro Asp Leu Thr Ala Cys Arg Thr Asn Asp Asp
 1               5                  10                  15

```
Gly Asp Thr Ala Val Val Ile Val Glu Lys Asp His Phe Met Asp Gly
                20                  25                  30

Phe Phe His Gln Val Glu Glu Ile Arg Ser Ser Ile Ala Arg Ile Ala
            35                  40                  45

Gln His Val Glu Asp Val Lys Lys Asn His Ser Ile Ile Leu Ser Ala
        50                  55                  60

Pro Asn Pro Glu Gly Lys Ile Lys Glu Glu Leu Glu Asp Leu Asn Lys
 65                  70                  75                  80

Glu Ile Lys Lys Thr Ala Asn Arg Ile Arg Gly Lys Leu Lys Ser Ile
                85                  90                  95

Glu Gln Ser Cys Asp Gln Asp Glu
            100

<210> SEQ ID NO 3
<211> LENGTH: 309
<212> TYPE: DNA
<213> ORGANISM: Homo sapiens

<400> SEQUENCE: 3
atgcgggacc ggctgccaga cctgacggcg tgtaggaaga atgatgatgg agacacagtt      60
gttgtggttg agaaagatca tttcatggat gatttcttcc atcaggtgga ggagattaga    120
aacagtattg ataaaataac tcaatatgtt gaagaagtaa agaaaaacca cagcatcatt    180
ctttctgcac caaacccgga aggaaaaata aagaagagc ttgaagatct gaacaaagaa     240
atcaagaaaa ctgcgaataa aattcgagcc aagttaaagg ctattgaaca aagttttgat    300
caggatgag                                                            309

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Histidine
      tag

<400> SEQUENCE: 4
atgcatcatc atcatcatca t                                               21
```